(12) United States Patent  (10) Patent No.: US 7,820,381 B2
Lemme et al.  (45) Date of Patent: Oct. 26, 2010

(54) METHOD AND APPARATUS FOR APPLYING FLUIDS TO A BIOLOGICAL SAMPLE

(75) Inventors: Charles Lemme, Oro Valley, AZ (US); Kurt Reinhardt, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 612 days.

(21) Appl. No.: 11/187,183

(22) Filed: Jul. 21, 2005

(65) Prior Publication Data

US 2006/0019302 A1  Jan. 26, 2006

Related U.S. Application Data

(60) Provisional application No. 60/590,843, filed on Jul. 23, 2004.

(51) Int. Cl.
*C12Q 1/68* (2006.01)
*G01N 33/53* (2006.01)
*G01N 35/00* (2006.01)
*C12M 1/34* (2006.01)
*C12M 3/00* (2006.01)

(52) U.S. Cl. .................. 435/6; 435/7.1; 435/287.1; 435/288.3; 436/46

(58) Field of Classification Search .............. 435/6, 435/7.1, 183, 287.1, 288.3; 436/46, 94; 536/23.1; 424/130.1
See application file for complete search history.

(56) References Cited

U.S. PATENT DOCUMENTS

| 4,146,414 | A | 3/1979 | Stormby |
| 4,203,797 | A | 5/1980 | Stormby |
| 4,359,013 | A | 11/1982 | Prevo |
| 4,392,450 | A | 7/1983 | Prevo |
| 5,024,933 | A * | 6/1991 | Yang et al. .................. 435/6 |
| 5,256,241 | A | 10/1993 | Noever |
| 5,308,460 | A * | 5/1994 | Mazid et al. ............... 435/14 |
| 5,355,439 | A | 10/1994 | Bernstein et al. |
| 5,425,918 | A | 6/1995 | Healey et al. |
| 5,595,707 | A | 1/1997 | Copeland et al. |
| 5,654,199 | A | 8/1997 | Copeland et al. |
| 5,737,499 | A | 4/1998 | Bernstein et al. |

(Continued)

FOREIGN PATENT DOCUMENTS

EP  0334534 B1  3/1994

(Continued)

*Primary Examiner*—Frank W Lu
(74) *Attorney, Agent, or Firm*—Klarquist Sparkman, LLP

(57) ABSTRACT

The invention is directed to a method of contacting a biological sample with a solution, comprising the steps of moving a curved surface wetted with the solution in proximity to the biological sample whereby the distance separating the wetted curved surface and the biological sample is sufficient to form a moving liquid meniscus layer between the two. The invention is also directed to an apparatus for contacting a biological sample suspected of containing a biomarker with a solution, comprising a platform for supporting a microscope slide having a biological sample thereon; a translating cap having a curved lower surface positioned above the platform, the curved lower surface being in proximity to a biological sample when in operation; means for moving the translating cap back and forth over the biological sample; and means for applying and removing liquid to and from the cap.

25 Claims, 6 Drawing Sheets

U.S. PATENT DOCUMENTS

| | | |
|---|---|---|
| 5,985,669 A | 11/1999 | Palander |
| 6,093,574 A | 7/2000 | Druyor-Sanchez et al. |
| 6,192,945 B1 | 2/2001 | Ford et al. |
| 6,296,809 B1 | 10/2001 | Richards et al. |
| 6,352,861 B1 | 3/2002 | Copeland et al. |
| 6,537,818 B2 | 3/2003 | Richards et al. |
| 6,544,798 B1 | 4/2003 | Christensen et al. |
| 2004/0058328 A1* | 3/2004 | Chan et al. ............. 435/6 |
| 2005/0074890 A1* | 4/2005 | Lemme et al. ........... 435/461 |
| 2005/0164374 A1 | 7/2005 | Kram |
| 2006/0019302 A1 | 1/2006 | Lemme et al. |
| 2008/0194034 A1 | 8/2008 | Erickson et al. |
| 2008/0286753 A1 | 11/2008 | Erickson et al. |
| 2009/0004691 A1 | 1/2009 | Erickson et al. |

FOREIGN PATENT DOCUMENTS

| | | |
|---|---|---|
| EP | 0590506 B1 | 12/1999 |
| EP | 0801732 B1 | 7/2005 |
| JP | 2004333346 A | 11/2004 |
| JP | 2004333347 A | 11/2004 |
| JP | 2004333349 A | 11/2004 |
| JP | 2004357698 A | 12/2004 |
| WO | WO96/21142 | 7/1996 |
| WO | WO 99/63342 | 12/1999 |
| WO | WO2005/064309 | 7/2005 |
| WO | WO2006/116035 | 11/2006 |
| WO | WO2006/116037 | 11/2006 |
| WO | WO2006/116039 | 11/2006 |
| WO | WO2006/116199 | 11/2006 |

* cited by examiner

METHOD AND APPARATUS FOR APPLYING FLUIDS TO A BIOLOGICAL SAMPLE

RELATED APPLICATION DATA

This claims the benefit of U.S. Provisional Patent Application No. 60/590,843, filed Jul. 23, 2004.

BACKGROUND

1. Field of the Invention

The invention is generally directed to the automation of biological sample processing, and is specifically directed to a method and apparatus for automated staining of biological samples using a low-volume tangential fluid approach.

2. Description of Related Art

Staining of biopsied tissue or cellular preparations for morphological visualization is an ancient art by modern standards that goes back over one hundred years. Recently, efforts have been made to automate the procedure of applying different types of chemical stains and biological conjugate molecules to tissue sections. Instruments that have been designed for this purpose include the Ventana Medical Systems' line of dual carousel-based instruments such as the 320/ES®, NexES®, BENCHMARK®, and the BENCHMARK® XT. Patents that describe these systems include U.S. Pat. Nos. 5,595,707, 5,654,199, 6,093,574, and 6,296,809, all of which are incorporated herein by reference in their entirety. Another type of automated stainer is the TechMate® line of stainers, described in U.S. Pat. Nos. 5,355,439 and 5,737,499, both of which are incorporated herein by reference in their entireties.

The rate of Immunohistochemical and in situ hybridization staining of sectioned fixed tissue on a microscope slide is limited by the speed at which the conjugating biomolecules can diffuse into the fixed tissue from an aqueous solution placed in direct contact with the tissue section. Typically, tissue is "fixed" immediately after excision by placing it in a 10% solution of formaldehyde, which preserves the tissue from autocatalytic destruction by cross-linking much of the protein via methylene bridges. This cross-linked tissue presents many additional barriers to diffusion including the lipid bilayer membranes that enclose individual cells and organelles, and the aforementioned effects of cross-linking that the fixation process generates. The conjugate biomolecules (antibody or DNA probe molecules) are relatively large, ranging in size from a few kilo Daltons to several hundred kiloDaltons, which constrains them to diffuse slowly into solid tissue with typical times for sufficient diffusion being in the range of several minutes to a few hours. Typical incubation conditions are thirty minutes at 37 degrees centigrade.

The diffusion rate is driven by a concentration gradient so the rate can be increased by increasing the concentration of the conjugate in the reagent. However, this has two detrimental effects. First, the conjugates are often very expensive, so increasing their concentration is wasteful and often not economically viable. Second, the excessive amount of conjugate that is driven into the tissue, when high concentrations are used, is entrapped in the tissue, and is difficult to rinse out and causes high levels of non-specific background staining. Non-specific staining is just noise. In order to reduce the noise and increase the signal of specific staining, current practice dictates using low concentrations of conjugate with long incubation times to allow the conjugate to find and bind to only the specific sites.

Automation of the previously manual processes of diffusion-driven staining has only increased these issues due to the necessarily larger pools of reagents. Present histology staining instruments use relatively large volumes of reagent (100 µl) in a puddle of typically 300 µl of buffer, as disclosed in issued U.S. Pat. Nos. 6,352,861, 6,296,809 and others. This produces a rather low concentration of the conjugate reagent in the puddle that resides over the tissue. Present instruments mix the reagent by alternating tangential air jets onto an overlaying oil layer that rotates and counterrotates when contacted by the alternating air jets, thereby imparting motion into the underlying aqueous puddle. This mixing is slow and not particularly vigorous, and creates evaporation issues that must be countered. The oil layer minimizes evaporation of the aqueous puddle by covering it with a layer of low vapor-pressure oil. Finally, present instruments use large volumes of rinse liquid to physically displace the reagent's large puddles of low concentration reagents which are covered with oil. This rinsing method produces large volumes of waste liquid which may be classified as hazardous waste, and in any event can physically disrupt the tissue by the vigorous washing action.

There continues to be a need for faster introduction of biomolecules into tissue sections for quicker processing and lower-volume reagent usage.

SUMMARY OF THE INVENTION

The embodiment is directed to a method of contacting a biological sample with a solution comprising the step of moving a curved surface wetted with a solution in proximity to said biological sample whereby the distance separating said wetted curved surface and said biological sample is sufficient to form a moving liquid meniscus layer between the two.

The invention is also directed to an apparatus for contacting a biological sample suspected of containing a biomarker with a solution containing a conjugate biomolecule, comprising a platform for supporting a microscope slide having a biological sample thereon; a translating cap having a curved lower surface positioned above the platform, the curved lower surface being in proximity to a biological sample when in operation; means for moving the translating cap back and forth over the biological sample; and means for applying and removing liquid solution containing the conjugate biomolecules to and from the cap.

DESCRIPTION OF THE PREFERRED EMBODIMENTS

Figure 1:
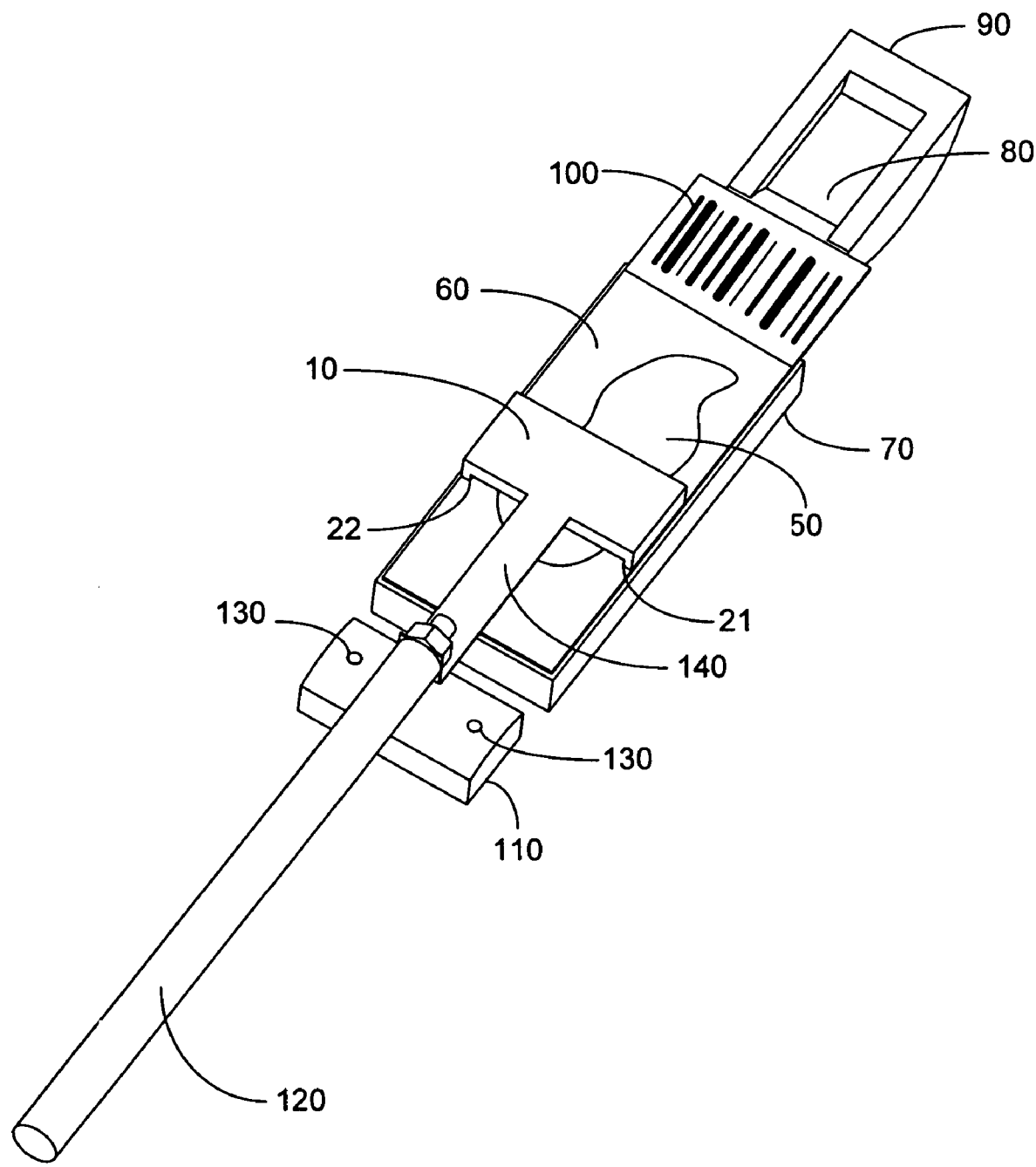
FIG. 1 is an elevational view from the right side.

The invention is directed to a method of contacting a biological sample suspected of containing a biomarker with a solution, comprising the step of moving a curved surface wetted with a solution containing the conjugate biomolecule in proximity to the biological sample whereby the distance separating the wetted curved surface and the biological sample is sufficient to form a moving liquid meniscus layer between the two.

The concept of the invention is relatively simple, yet elegant. With respect to the figures generally, there is placed over the microscope slide 60 a curved surface 30 in close proximity, about 10-100 microns, from the slide surface. Since the thickest section of tissue or biological sample 50 is usually 4-6 microns, and at most 32 microns thick, this leaves significant clearance for the curved surface 30 to move without touching the tissue 50. The curved surface 30 is part of a larger structure called a "translating cap 10," which may be about 10 mm long with a 25 mm radius on its bottom. A small volume of liquid reagent 40 forms a meniscus along the length of the slide in the gap between the tissue and curved surface of the cap. During incubation, the cap "translates," or moves back and forth, along the length of the slide, pulling the meniscus back and forth over the useful area of the slide that contains the biological sample. The faster the velocity of the cap, the more mixing that will occur. The cap may be heated so that liquids adhering to it are also heated.

Rinsing is accomplished by moving the cap off the end of the slide so that the meniscus touches a fixed surface, a rinse pad or block 110 which is curved in the opposite direction from the cap and which, through capillary action, wicks the fluid off the cap. Rinse solution is added to the bottom of the cap through vertical holes, 130, in the rinse block, 110. This flow of rinse solution, cleans the cap and some of this solution adheres to the cap by surface tension. The cap is then moved back over the slide carrying the rinse solution with it which then mixes with liquid remaining on the slide. Repeating this a few times cleans the slide by serial dilution.

Total cleansing of the cap can be done after the slide is removed by addition of a strong agent, say pH 14 NaOH, to the heater surface and translating the cap through it a few times. Then the heater/cap is rinsed with normal rinse solution. This will remove any remnants of the tissue from the previous slide and prevent cross contamination between slides.

Certain definitions will now be discussed which are to be used when interpreting the claims and their proper scope. Undefined terms should be given their usual and customary meaning, unless from the context it is apparent some divergent meaning should attach.

The term "conjugate biomolecule" is used to describe any biomolecule that has an ability to specifically locate and bind to its complementary surface. Examples include an antibody which specifically binds to its complementary epitope, a RNA or DNA probe which hybridizes to its complementary sequence under hybridizable conditions, or a chemical stain which preferentially stains a particular protein such as keratin. Although chemical stains are not generally considered biomolecules, for the purpose of this application it is included as such. They are generally referred to as "special stains" in the histology art.

The term "biological sample" may be used generally to refer to any biological material which may be placed on a microscope slide or similar substantially horizontal format. Included as illustrative biological samples are tissue sections, cellular preparations such as cytopins or ThinPrep™s (Cytyc, Marlborough, Mass.), or tissue or nucleic acid microarrays.

The term "biomarker" is intended to mean the plethora of biological target molecules that may detected that are in some way associated with a pathological condition. Included as illustrative examples are antigens, epitopes, cellular proteins, transmembrane proteins, and DNA or RNA sequences. The Her-2/neu gene and protein are both illustrative examples of biomarkers.

This method is applicable to other common Immunohistochemical processes such as deparaffinization, antigen retrieval, and detection (cell conditioning). For deparaffinization using the aqueous process described in U.S. Pat. No. 6,544,798B1 (aqueous deparaffinization using heat), incorporated herein by reference, heat would have to be supplied to heat either the aqueous solution that bathes the biological sample above the melting point of paraffin, or a heater built into the slide support could directly heat the slide/tissue. The heat must be sufficient to heat the sample above the melting point of paraffin to release the paraffin into the immiscible aqueous phase where it is then removed. Alternatively, deparaffinization that requires the use of a paraffin solvent such as xylene or limonene could be performed using this apparatus.

Cell conditioning to make the cross-linked antigenic sites more accessible by large biomolecules such as antibodies and nucleic acid probes can also be performed using this method and apparatus. Applying heat to the sample is one way to cell condition, therefore heat in some format would need to be supplied to the sample. In addition to the previously-described slide-support heater, heat can be applied by direct application (conduction), indirect conduction (thought the microscope slide), convection (heated air directed onto the sample), or radiantly (infrared or microwave). Presently indirect conduction is preferred. Cell conditioning is typically performed by incubating the tissue sample from 75-100 degrees C. in an aqueous solution and holding it for some period until adequate antigenicity is attained, typically 30-90 minutes.

The invention is also directed to apparatus for performing the method. The apparatus can generally be described with regard to the following figures and accompanying text, which depicts the overall concept of the invention.

Figure 2:
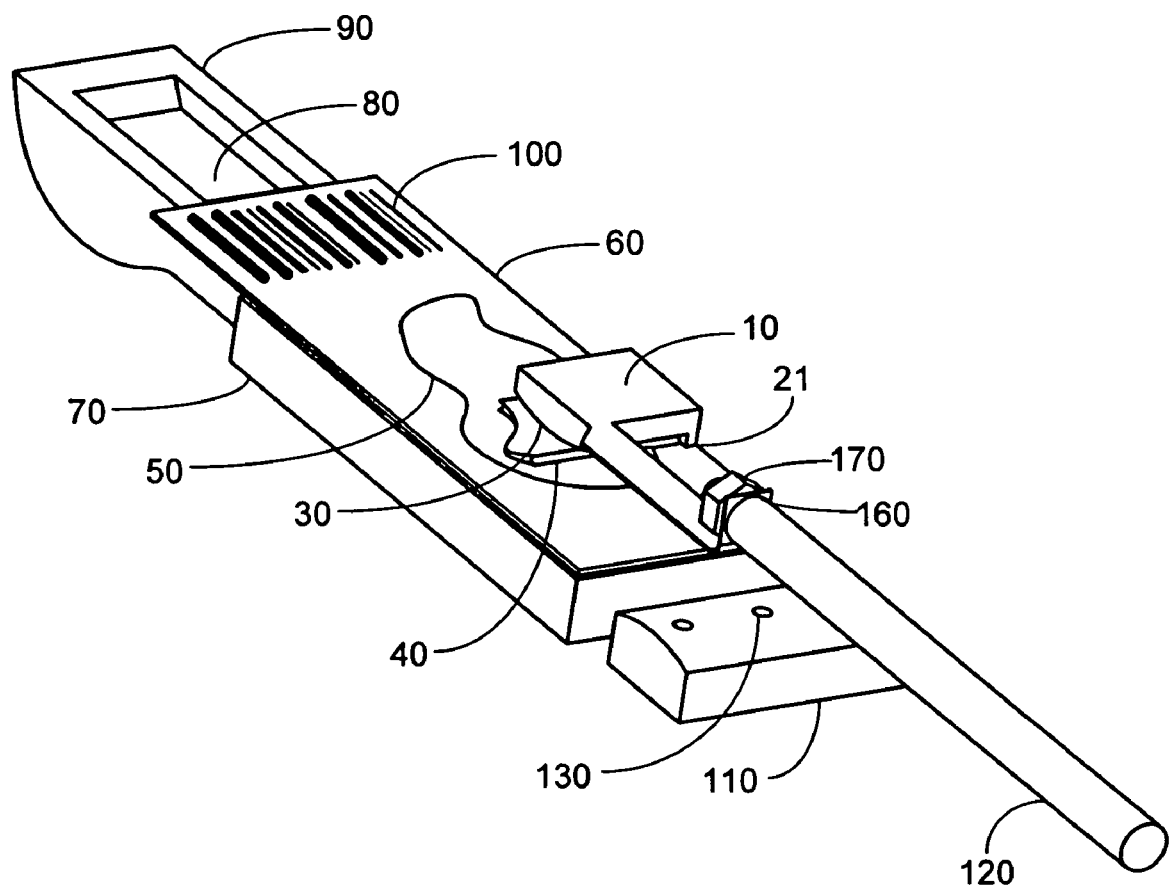
FIG. 2 is an alternate elevational view from the left side, partially sectioned through the middle of the cap.
Figure 3:
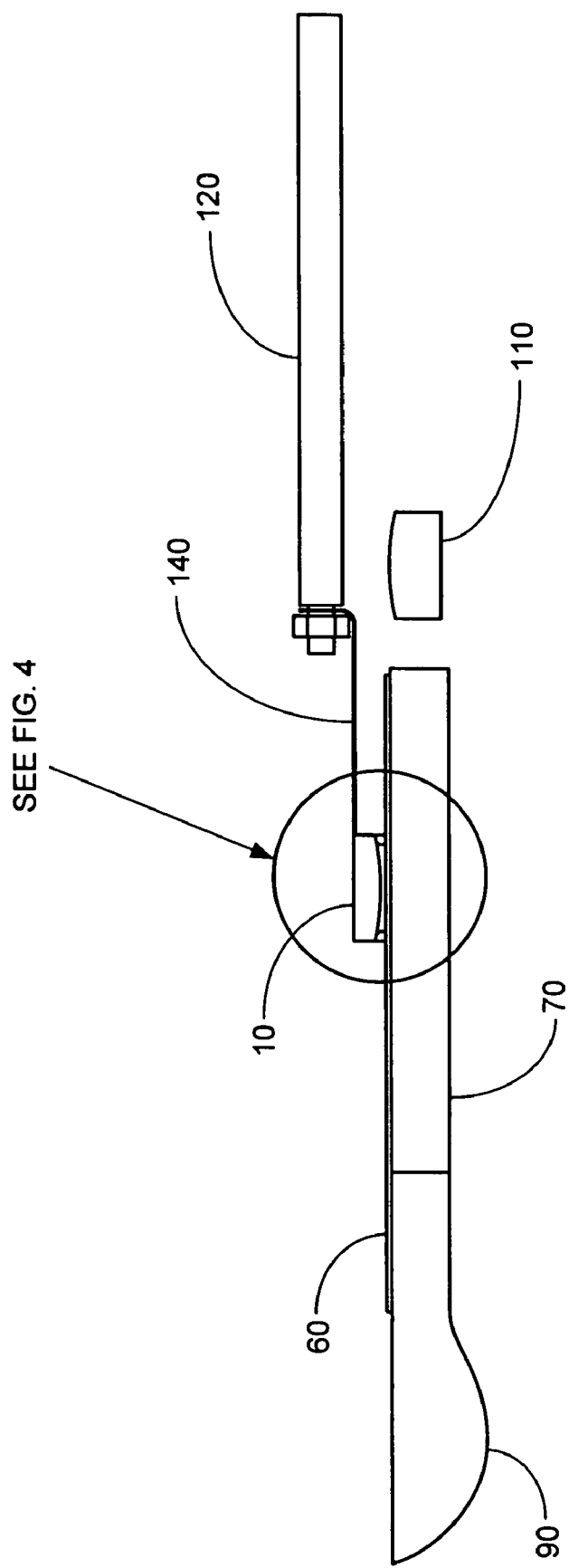
FIG. 3 is a cross-sectional view from the left side, again partially sectioned through the cap.
Figure 4:
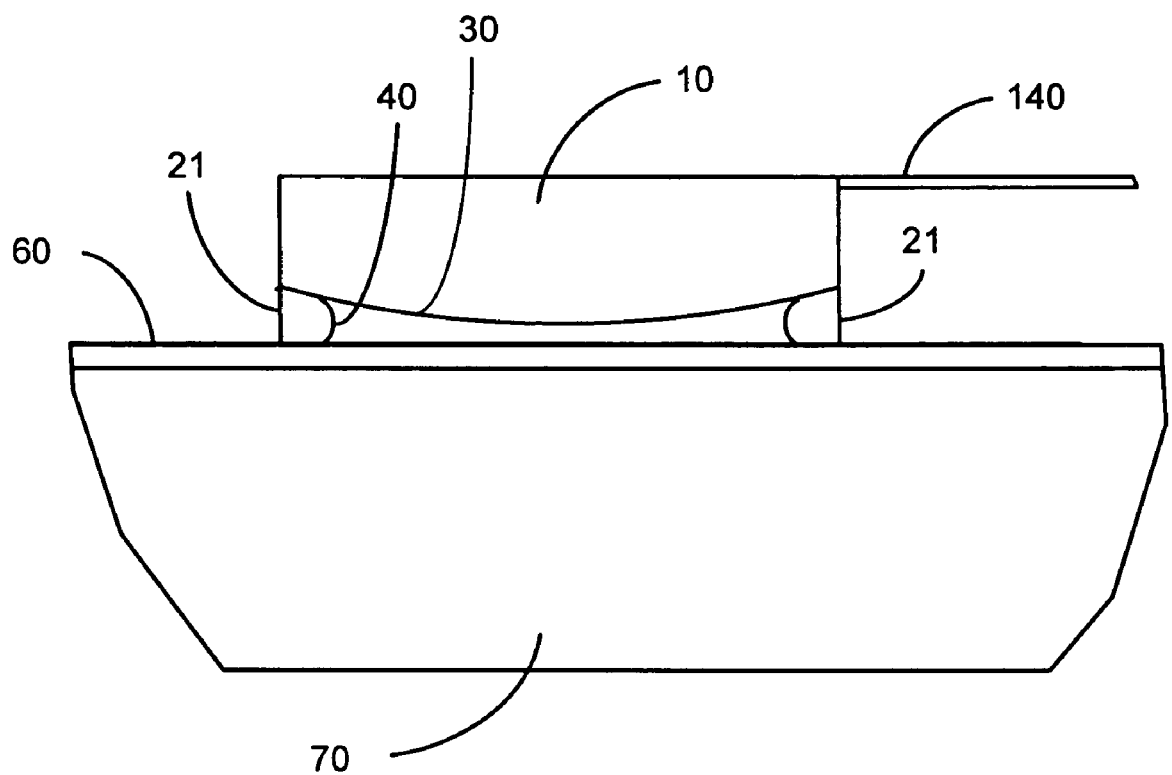
FIG. 4 is a detail of the sectioned area of the translating cap, the retained reagent and its meniscus.

FIGS. 1-4 show the preferred embodiment of the translating curved cap invention. FIGS. 1 and 2 are elevational views from the right and left sides. FIG. 3 is a cross-sectional view from the left side and FIG. 4 is a detail of the sectioned area of the translating cap, the retained reagent and its meniscus. Translating cap 10 is sectioned at its middle to show the liquid reagent 40 that is retained by surface tension under the cap 10.

The cap may be made from many different types of materials, however most preferred are plastics, particularly ULTEM™ (General Electric), and ceramics including glass. The material that will be holding the reagent liquid must be wettable and cleanable given the range of biomolecules that it will be applying, like chemicals, proteins and nucleic acids. In the preferred embodiment the curved surface is convex with respect to the microscope slide surface. A convex shape creates the correct angle with the slide and sample surface so that an optimal meniscus is formed. The cap may be as wide as the slide, but in any event should cover substantially all of the sample surface. The curved surface 30 is moved in a substantially rectilinear fashion parallel to the microscope slide's upper surface and over the biological sample's surface. Typically the distance separating the wetted curved surface 30 and the biological sample is from about 15 microns to about 45 microns.

In an alternate embodiment, the cap may be electrically conductive so that is can conduct current through the tissue when the cap is positioned in proximity to it, and is in electrical contact through an electrolytic solution. The benefit of electrical conductivity is that an electrophoretic effect can be imparted that allows charged molecules to be driven into the tissue via electrophoresis.

Cap 10 has two sliding guides 21, 22 at its lateral extremes, both of which are only shown together in FIG. 1. These guides rest on the top, outer edge of the microscope slide 60 and are about 0.5 mm wide, although the exact width is not critical. They position the cap vertically and determine the gap that exists between the top of the slide and the bottom of the center curved portion of the cap 30, best shown in FIGS. 2 and 4. Only one sliding guide, 21, is shown in FIGS. 2 and 4 because of the cross-sectioning of the cap. It is preferred that no tissue be on this outer one-half millimeter of the slide 60 where these guides rest. In FIGS. 2-4, the cap is sectioned at its middle to show the curved surface 30 that spans the distance between the two sliding guides. This curved surface 30 in this embodiment has a 25 mm radius and is positioned about 50 microns above the bottom of the sliding guides 21, 22. This produces a 50-micron gap between the bottom of the curved surface 30 and the top of slide 60. The 50-micron gap is determined by the vertical extension of the sliding guides 21 and 22 below the bottom of the curved surface 30 of the cap 10. Biological sample or tissue 50 is adhered to the slide 60 and is typically less than eight microns in thickness unless it is very soft tissue, such as brain, in which case it can be as much as 35 microns. The 50 micron gap allows the cap 10 to slide over any reasonable thickness of tissue 50. When the cap is retracted off of the slide 60 and resting on the rinse pad 110, reagent liquid 40 is applied to the top of the slide from a pipette (not shown) in small quantities, say 15 µl. An automated pipettor such as described in U.S. Pat. No. 6,537,818B2, incorporated herein by reference, is one such example. Other dispenser designs may be used with equal effect such as an inline dispenser as disclosed in U.S. Pat. No. 6,192,945, incorporated herein by reference. When the cap 10 is returned to the slide 60, the reagent liquid 40 is attracted to the curved bottom surface of the cap 30 where it adheres by capillary action. It forms a meniscus at each end that is best shown at 40 in FIG. 4.

Cap 10 is oscillated longitudinally ("translated") along the length of the slide 60 by a rod 120 that is attached to vertically flexible section 140 which in turn is attached to the center of the cap 10. Rod 120 in turn is activated by a powering mechanism such as a pressure or vacuum-driven air cylinder, motor driven screw, or other conventional means of mechanically urging a component back and forth in a single plane, not shown. Both gliding edges 21 and 22 are in contact with the slide. It is desireable that there be some mechanism to provide for positive contact of the cap with the slide. The method used in one preferred embodiment is to attach the cap by means of a vertically flexible section 140 which is placed between the rod 120 and the cap 10. The vertically flexible section is attached to the driving rod 120 by a joint that is free to rotate around the axis of the rod 120. These two degrees of freedom, vertical and axial rotation, allows the cap to always be in contact with the slide, regardless of manufacturing tolerances that may tend to lift it off of the slide. Flexible section 140, in the preferred embodiment, is made of a thin section of 302 stainless steel that is approximately 0.15 mm thick by 10 mm wide by 25 mm long. This flexible section 140 is stiff in all directions except vertically and allows the cap 10 to be pulled by gravity downward onto the slide. Flexible section 140 is attached to rod 120 by passing through a hole 150 in its far end that is bent upward 160 and retained by a nut 170. In the drawings, hole 160 is in the vertical section 160 of the vertically flexible section 140, but is not visible in these figures. It can be seen, however, that rod 120 passes through hole 150. Other means of keeping the cap in continuous contact with the surface of the slide abound, including using a spring-loaded armature such as a shock absorber that in normal operation pushes the cap gliding edges into contact with slide surface. One of ordinary skill can implement many such positive-contact solutions, all of which are well within the skill of the art.

The cap is oscillated back and forth along the slide so that the curved bottom surface of the cap 30 at its extreme limits, is a few mm from the end of the slide at one extreme and a few mm from the bar code label 100 at its other extreme. Much of the reagent fluid is trapped under the moving cap, but some may be left on the surface of the slide, over the tissue. The moving cap always carries some reagent with it, and mixes it with the layer that is left on the surface of the tissue. In this way, the reagent is continuously, vigorously mixed by having to pass through the narrow passage between the slide and the bottom of the curved portion of the cap. The surface chemistry of the slide surface in contact with the biological sample may be modified to make it either more hydrophobic or more hydrophilic, thereby affecting the amount of liquid left on the slide surface. For instance, when using an aqueous solution and assuming a hydrophilic cap surface, a more hydrophobic slide surface will encourage the solution to stay within the space demarcated by the cap and the slide surface, as the cap will be hydrophilic, and the aqueous solution will be repelled by the hydrophobic slide. Conversely, a hydrophilic slide surface will spread the solution more over the slide surface, resulting in more "puddles" on the slide. One of ordinary skill will be able to determine, without undue experimentation, the optimal surface characteristics to use.

Specifically in relation to FIG. 2, in order to rinse the reagent liquid off of the slide, the cap is retracted all the way to be on top of the rinse block 110. The top of the rinse block is curved in the opposite direction from the bottom of the cap with a radius of about 25 mm. Rinse fluid is pumped up through the rinse holes 130 which rinses the curved bottom surface 30 of the cap 10 and leaves a volume of rinse fluid attached to it. The cap is then oscillated once over the length of the slide, where it mixes the rinse fluid on the cap with the fluid that remains on the slide. The cap is again returned to the rinse block and rinsed with clean rinse solution. This process is repeated multiple times providing a serial dilution of the liquid on the slide. Even if the dilution is only 50%, there will be a million times dilution in 20 stokes. All the excess fluid from rinses flow by gravity to the bottom of the chamber, not shown, where it runs out a waste tube, again not shown.

Most reactions that are used for histology require an elevated temperature, from 40° to over 90° C. The thin layer of aqueous reagent that is left on the surface of the slide would evaporate if the humidity is less than 100%. There are at least two solutions. One could continuously add pure water back into the reagent mechanically, that is, dispense liquid water out of a nozzle/pipettor/dispenser. Another method is to keep the humidity around the slide at 100%. A heated humidified chamber would be necessary to counteract the drying of the biological sample if it is to be exposed to heat to perform in situ hybridization reactions, cell conditioning, or heat-based deparaffinization. In regard to FIGS. 1-4, in the preferred embodiment the entire mechanism is enclosed in an insulated chamber, not shown. The chamber has a door at one end, through which the microscope slide is inserted, also not shown. The slide is heated by a profiled resistive heater 70, such as that disclosed in U.S. Pat. No. 6,296,809, incorporated herein by reference. At the bar code 100 end of the slide, heater 70 has an extension that is under a cup or reservoir, 90. The heater portion under the cup is set to always be about five degrees Celsius above the temperature of the aqueous puddle of reagent on the slide. The heated cup contains a few milliliters of water 80. This hot water is always evaporating, filling the chamber with warm water vapor so that vapor condenses back onto the wet slide as fast as it evaporates, so that there is no net loss of water from the reagent puddle. Some water will condense on the interior surface of the chamber, heating it to the temperature of the water in the cup 90. To minimize the heat loss from the chamber, it must be well-insulated.

Figure 5:
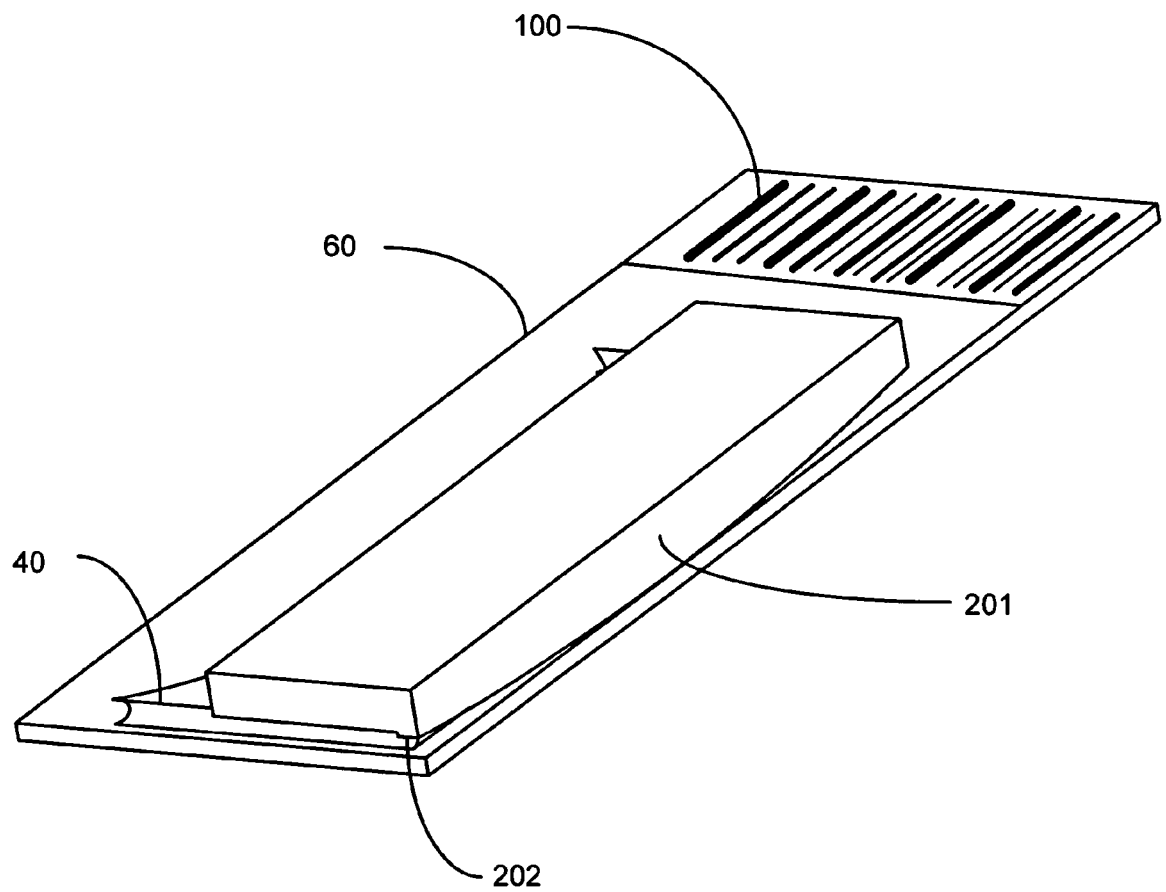
FIG. 5 is an elevational view of an alternate embodiment showing a rocking cap on a slide.

In another embodiment shown in FIG. 5, the cap may be elongated along its curved axis so that it does not need to be driven by a rod back and forth over the biological sample. Instead, it is rocked so that the meniscus layer shifts back and forth under the rocking curved surface as shown in FIG. 5 where 201 is the rocking cap and 202 is an outer rail that is about 50 microns high and is equivalent in function to the sliding guides 21 and 22 of FIGS. 1, 2 and 4.

Figure 6:
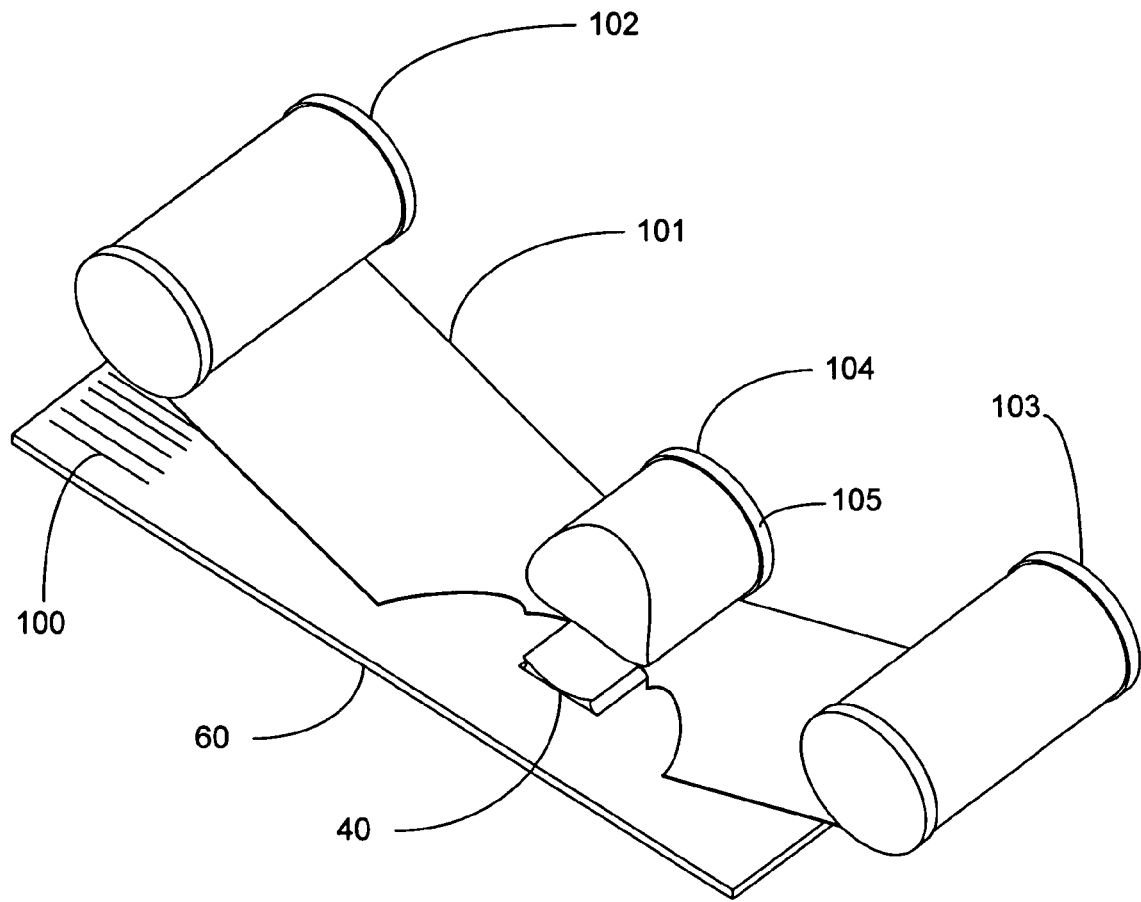
FIG. 6 is an elevational view of an alternate embodiment showing a membrane-based contact mechanism including a storage drum, a take-up drum and a rolling cap.

A further embodiment shown in FIG. 6 is to oscillate a surface over a membrane that can be changed from one slide to another, as show in FIG. 6 where 101 is a membrane that can be changed from one slide to the next by unrolling from storage drum 103 and pulled onto take-up drum 102. During operation, rolling cap 104 translates and rolls along the slide, held off by spacer lips, 105 which are about 50 microns plus the thickness of the membrane high and are equivalent in function to the sliding guides 21 and 22 of FIGS. 1, 2 and 4. The advantages of this embodiment include being able to use a fresh contact surface on alternate runs, thereby minimizing cross contamination of reagents.

All of the actions described herein may be controlled in an automatic manner by appropriate design of a computerized interface capable of controlling said operations. Examples of automated computer-controlled staining instruments include the Ventana family of instruments mentioned previously, in particular the BENCHMARK® line, described in U.S. Pat. No. 6,296,809B1, incorporated herein by reference.

Although certain presently preferred embodiments of the invention have been described herein, it will be apparent to those skilled in the art to which the invention pertains that variations and modifications of the described embodiments may be made without departing from the spirit and scope of the invention. For instance, although a rounded cap has been disclosed for the curved surface, it is contemplated that other structures such as spheres, hemispheres, or cylinders may also be used. Accordingly, it is intended that the invention be limited only to the extent required by the appended claims and the applicable rules of law.

We claim:

1. A method of contacting a biological sample with a solution, comprising:
    contacting said biological sample with said solution, said biological sample being mounted on a surface of a microscope slide and said solution forming a solution layer covering at least a portion of said biological sample; and
    moving, directly and repeatedly, a curved surface wetted with said solution in proximity to said biological sample such that the wetted curved surface contacts said solution layer and mixes said solution on said wetted curved surface with said solution of said solution layer, said wetted curved surface being separated from said surface of said microscope slide at a distance such that a liquid meniscus layer forms in the solution layer between said wetted curved surface and said surface of said microscope slide.

2. The method of claim 1 wherein said solution contains a conjugate biomolecule selected from the group consisting of an antibody, a RNA/DNA probe, or a chemical stain or a chemical used in detection.

3. The method of claim 1 wherein said biological sample is a tissue section or a cellular preparation or an array of RNA/DNA or a tissue or a protein or a peptide.

4. The method of claim 1 wherein said biological sample is a tissue section and said tissue section contains a biomarker which is an antigen or an epitope or a cellular protein or a DNA/RNA sequence.

5. The method of claim 1 wherein said curved surface is made from metal or plastic or ceramic.

6. The method of claim 1 wherein said curved surface is convex with respect to said surface of said microscope slide.

7. The method of claim 1 wherein said curved surface is moved in a rectilinear fashion substantially parallel to said surface of said microscope slide and above a surface of said biological sample.

8. The method of claim 1 wherein said distance separating said wetted curved surface and said surface of said microscope slide is from about 10 microns to about 100 microns.

9. The method of claim 1 wherein said moving said curved surface comprises rocking said curved surface so that said liquid meniscus layer shifts back and forth across said biological sample.

10. The method of claim 1 wherein said moving said curved surface comprises moving said curved surface back and forth above said biological sample.

11. The method of claim 1 further comprising moving said wetted curved surface away from said surface of said microscope slide and contacting said wetted curved surface with a fixed surface that wicks said solution from said wetted curved surface.

12. The method of claim 11 further comprising adhering a rinse solution to said curved surface while said curved surface is in proximity to said fixed surface and moving said curved surface having said rinse solution adhered thereto back above said surface of said microscope slide, thereby mixing said rinse solution adhered to said curved surface with said solution remaining on said microscope slide.

13. The method of claim 1 further comprising heating said curved surface.

14. An automated method of contacting a biological sample with a solution, comprising:
    contacting said biological sample with said solution, said biological sample mounted on a surface of a microscope slide and said solution forming a solution layer covering at least a portion of said biological sample; and
    moving, directly and repeatedly, under computer control, a curved surface wetted with said solution back and forth above said biological sample such that the wetted curved surface contacts said solution layer and mixes said solution on said wetted curved surface with said solution of said solution layer, said wetted curved surface being separated from said surface of said microscope slide at a distance such that a liquid meniscus layer forms in the solution layer between said wetted curved surface and said surface of said microscope slide.

15. The method of claim 14 wherein said solution contains a conjugate biomolecule selected from the group consisting of an antibody, a RNA/DNA probe, or a chemical stain or a chemical used in detection.

16. The method of claim 14 wherein said biological sample is a tissue section or a cellular preparation or an array of RNA/DNA or a tissue or a protein or a peptide.

17. The method of claim 14 wherein said biological sample is a tissue section and said tissue section contains a biomarker which is an antigen or an epitope or a cellular protein or a DNA/RNA sequence.

18. The method of claim 14 wherein said curved surface is made from metal or plastic or ceramic.

19. The method of claim 14 wherein said curved surface is convex with respect to said surface of said microscope slide.

20. The method of claim 14 wherein said curved surface is moved in a rectilinear fashion substantially parallel to said surface of said microscope slide and above a surface of said biological sample.

21. The method of claim 14 wherein said distance separating said wetted curved surface and said surface of said microscope slide is from about 10 microns to about 100 microns.

22. The method of claim 14 wherein said moving said curved surface further comprises rocking said curved surface so that said liquid meniscus layer shifts back and forth across said biological sample.

23. The method of claim 14 further comprising moving said wetted curved surface away from said surface of said microscope slide and contacting said wetted curved surface with a fixed surface that wicks said solution from said wetted curved surface.

24. The method of claim 23 further comprising adhering a rinse solution to said curved surface while said curved surface is in proximity to said fixed surface and moving said curved surface having said rinse solution adhered thereto back above said surface of said microscope slide, thereby mixing said rinse solution adhered to said curved surface with said solution remaining on said microscope slide.

25. The method of claim 14 further comprising heating said curved surface.

* * * * *